United States Patent
Park et al.

(10) Patent No.: US 9,943,831 B2
(45) Date of Patent: Apr. 17, 2018

(54) METHOD FOR PREPARING FERRITE METAL OXIDE CATALYST

(71) Applicant: Korea Kumho Petrochemical Co., Ltd., Seoul (KR)

(72) Inventors: Ji Won Park, Daejeon (KR); Jae Woo Kim, Daejeon (KR); Yong Hee Yun, Daejeon (KR); Yun Jung Kim, Daejeon (KR); Kyoung Ho Row, Daejeon (KR)

(73) Assignee: Korea Kumho Petrochemical Co., Ltd., Seoul (KR)

( * ) Notice: Subject to any disclaimer, the term of this patent is extended or adjusted under 35 U.S.C. 154(b) by 92 days.

(21) Appl. No.: 14/876,356

(22) Filed: Oct. 6, 2015

(65) Prior Publication Data

US 2016/0354764 A1 Dec. 8, 2016

(30) Foreign Application Priority Data

Jun. 5, 2015 (KR) ........................ 10-2015-0079758

(51) Int. Cl.
*B01J 23/78* (2006.01)
*B01J 37/04* (2006.01)
(Continued)

(52) U.S. Cl.
CPC .............. *B01J 23/78* (2013.01); *B01J 37/04* (2013.01); *B01J 37/082* (2013.01); *C07C 5/48* (2013.01);
(Continued)

(58) Field of Classification Search
CPC .......... B01J 23/78; B01J 37/04; B01J 37/082; C07C 2523/78; C07C 5/48
See application file for complete search history.

(56) References Cited

U.S. PATENT DOCUMENTS

2006/0106268 A1* 5/2006 Kowaleski ............. B01J 23/745
  585/444
2008/0200739 A1* 8/2008 Walsdorff ............. B01J 23/745
  585/250

(Continued)

OTHER PUBLICATIONS

Machine translation of KR101340621 B1, Park et al., dated Dec. 11, 2013.*

*Primary Examiner* — Jun Li
(74) *Attorney, Agent, or Firm* — Saliwanchik, Lloyd & Eisenschenk

(57) ABSTRACT

One aspect of the present invention provides a method for preparing a ferrite metal oxide catalyst, comprising (a) preparing a precursor solution by dissolving a magnesium nitrate precursor and an iron nitrate precursor in a polar solvent, (b) forming a catalyst powder by spray-pyrolyzing the precursor solution into a reactor using a carrier gas, and (c) calcinating the catalyst powder in a reservoir after conveying the catalyst powder to the reservoir. The method may increase the activity and stability of a catalyst powder by additionally performing a step of calcinating the catalyst powder at a certain temperature for a certain period of time, and may increase the purity of the catalyst by reducing moisture and nitrate remaining in the catalyst. Also, when using the catalyst in an oxidative dehydrogenation of n-butene, the selectivity and purity of 1,3-butadiene may increase.

6 Claims, 3 Drawing Sheets

(51) Int. Cl.
*B01J 37/08* (2006.01)
*C07C 5/48* (2006.01)
(52) U.S. Cl.
CPC .... *C07C 2523/745* (2013.01); *C07C 2523/78* (2013.01)

(56) References Cited

U.S. PATENT DOCUMENTS

| 2013/0217568 A1* | 8/2013 | Hazin | B01J 27/138 |
| | | | 502/226 |
| 2014/0141965 A1* | 5/2014 | Xiong | C07C 5/48 |
| | | | 502/213 |
| 2016/0184806 A1* | 6/2016 | Xiong | B01J 23/8892 |
| | | | 502/329 |

* cited by examiner

METHOD FOR PREPARING FERRITE METAL OXIDE CATALYST

CROSS-REFERENCE TO RELATED APPLICATION

This application claims the benefit under 35 U.S.C. § 119 of Korean Application No. 10-2015-0079758, filed Jun. 5, 2015, which is hereby incorporated by reference in its entirety.

BACKGROUND

Field of the Invention

The present invention relates to a method for preparing a ferrite metal oxide catalyst.

Discussion of Related Art

A divalent cation contained in a ferrite metal oxide catalyst associated with an oxidative dehydrogenation of n-butene affects the yield of a reaction product, 1,3-butadiene. In particular, zinc ferrite, manganese ferrite, and magnesium ferrite are known to have higher selectivity for 1,3-butadiene than other types of metal ferrite.

When carrying out the oxidative dehydrogenation of n-butene, the conventional ferrite metal oxide catalyst was prepared by physical mixing and co-precipitation method. Such co-precipitation method is commonly used for preparing a metal oxide catalyst. However, this method is uneconomic because it includes multiple steps, and it produces a large amount of waste in filtering and washing processes after preparing the catalyst.

In this regard, Korean Patent No. 10-1340621 simplified the method for preparing the catalyst by using a spray-pyrolysis process. However, the catalyst has low stability because it is processed at high temperature for short period of time, and purity of the catalyst is decreased because a large amount of by-products, such as moisture, nitrates, etc., remains in the prepared catalyst.

SUMMARY OF THE INVENTION

To solve the problems, there is provided a method for preparing a ferrite metal oxide catalyst with increased purity and structural stability, and a method for preparing 1,3-butadiene using the ferrite metal oxide catalyst prepared thereby.

One aspect of the present invention provides a method for preparing a ferrite metal oxide catalyst, comprising (a) preparing a precursor solution by dissolving a magnesium nitrate precursor and an iron nitrate precursor in a polar solvent, (b) forming a catalyst powder by spray-pyrolyzing the precursor solution into a reactor using a carrier gas, and (c) calcinating the catalyst powder in a reservoir after conveying the catalyst powder to the reservoir.

In one embodiment, the magnesium nitrate precursor and iron nitrate precursor in step (a) may be mixed so that molar ratio of magnesium to iron is 1.5:1 to 2.5:1.

In one embodiment, the magnesium nitrate precursor and iron nitrate precursor in step (a) each may be magnesium nitrate and iron nitrate.

In one embodiment, the polar solvent in step (a) may be distilled water.

In one embodiment, the carrier gas in step (b) may be air.

In one embodiment, pressure of the air in step (b) may be 2 to 4 atm.

In one embodiment, the pyrolysis temperature in step (b) may be 500° C. to 900° C.

In one embodiment, the calcination temperature in step (c) may be 500° C. to 600° C.

In one embodiment, the calcination in step (c) may be carried out for 1 to 4 hours.

Another aspect of the present invention provides a ferrite metal oxide catalyst prepared by the method.

Still another aspect of the present invention provides a method for preparing 1,3-butadiene, comprising filling the ferrite metal oxide catalyst in a reactor, and introducing a reaction mixture containing n-butene into the reactor to pass through the reactor.

In one embodiment, the reaction mixture may comprise 4 to 12% by volume of n-butene, 16 to 30% by volume of air, and 60 to 80% by volume of steam.

In one embodiment, the reaction mixture may be introduced in gas hourly space velocity (GHSV) in range of 100 $h^{-1}$ to 700 $h^{-1}$.

In one embodiment, temperature of the reactor may be controlled to be 300° C. to 500° C.

The method for preparing a ferrite metal oxide catalyst according to one aspect of the present invention may increase activity and stability of a catalyst powder by additionally performing a step of calcinating the catalyst powder at a certain temperature for a certain period of time, and may increase purity of the catalyst by reducing moisture and nitrate remaining in the catalyst.

Also, when using the catalyst prepared by additionally performing the calcination step in an oxidative dehydrogenation of n-butene, selectivity and yield of 1,3-butadiene may increase.

The effect of the present invention is not limited to the above effects, but it should be understood that the present invention includes all of the effects which can be deduced from the present invention described in the detailed description or the claims of the present invention.

DETAILED DESCRIPTION OF EXEMPLARY EMBODIMENTS

Exemplary embodiments of the present invention will be described in detail below with reference to the accompanying drawings. However, the present invention may be realized in various different forms, and therefore is not limited to examples to be described herein. In addition, to clearly explain the present invention, parts not relating to the descriptions will be omitted, and like reference marks denote the like parts throughout the specification.

In the specification, when one part "includes" a component, unless particularly described otherwise, it means that the part can further include a different component, not excluding the component.

Hereinafter, examples of the present invention will be described in detail with reference to the accompanying drawings.

Figure 1:
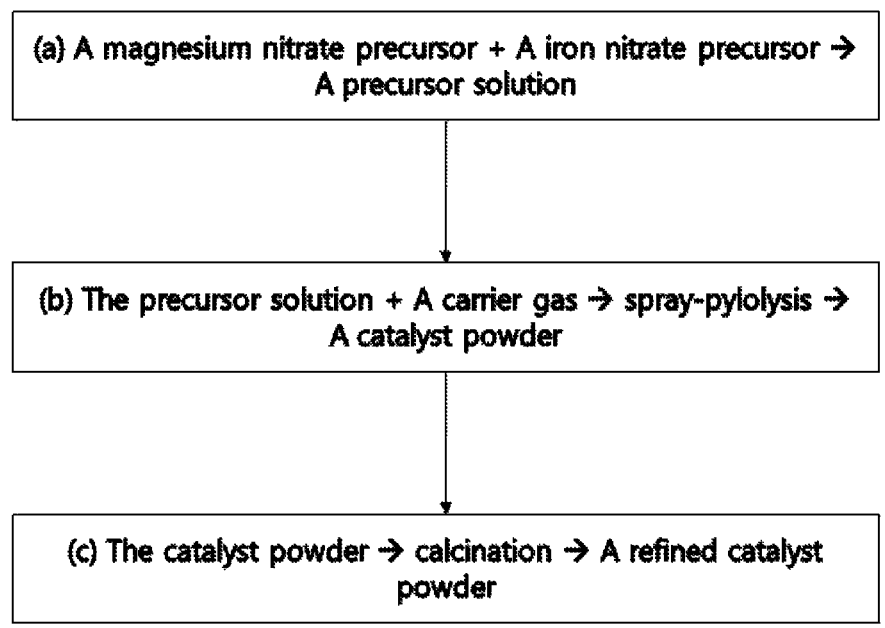
FIG. 1 is a schematic diagram illustrating a method for preparing a ferrite metal oxide catalyst according to one embodiment of the present invention.

FIG. 1 is a schematic diagram illustrating a method for preparing a ferrite metal oxide catalyst according to one embodiment of the present invention.

Referring to FIG. 1, the method for preparing a ferrite metal oxide catalyst according to one embodiment of the present invention may include (a) preparing a precursor solution by dissolving a magnesium nitrate precursor and an iron nitrate precursor in a polar solvent, (b) forming a catalyst powder by spray-pyrolyzing the precursor solution into a reactor using a carrier gas, and (c) calcinating the catalyst powder in a reservoir after conveying the catalyst powder to the reservoir.

In order to increase solubility of the precursor in step (a), temperature of the solution may be controlled to be 10° C. to 80° C., preferably from 15° C. to 60° C., and more preferably from 25° C. to 40° C.

The magnesium nitrate precursor and the iron nitrate precursor may be mixed so that molar ratio of magnesium to iron is 1.5:1 to 2.5:1. When the molar ratio of magnesium to iron is controlled to be the above range, surface area and weight loss of the ferrite metal oxide catalyst may be 60 to 100 m$^2$/g and may be 20% by weight or less, respectively. When the surface area of the catalyst is less than 60 m$^2$/g, the contact area between n-butene and the catalyst decreases, thereby decreasing the selectivity of 1,3-butadiene, and when the surface area is greater than 100 m$^2$/g, the contact time increases, thereby increasing the amount of byproducts. Further, when the weight loss is greater than 20% by weight, the stability and activity of the catalyst may decrease.

The magnesium nitrate precursor and the iron nitrate precursor may be nitrate magnesium and nitrate iron, respectively, but are not limited thereto. Also, instead of each nitrate precursor, at least one selected from the group consisting of sulphate precursor, chloride precursor, and carbonate precursor may be used.

The polar solvent may be distilled water, but is not limited thereto. When the polar solvent is distilled water, purity of the final product, i.e., the ferrite metal oxide catalyst may increase by minimizing impurities in the precursor solution.

The carrier gas in step (b) may be air, and the pressure of the air may be 2 to 4 atm, and preferably 3 atm. When the pressure of the air is less than 2 atm, the particle size of the catalyst powder may increase and the surface area may decrease, and then selectivity of 1,3-butadiene may decrease. When the pressure is greater than 4 atm, the cost may increase, thereby being uneconomic, and a high melt may be formed or the crystal structure may change arbitrarily, thereby decreasing the activity of the catalyst.

The pyrolysis temperature in step (b) may be 500° C. to 900° C., preferably 700° C. to 800° C., and more preferably 750° C. When the pyrolysis temperature deviates from the above range, the catalyst melts, forming a high melt, or the crystal structure of the catalyst may change arbitrarily. When carrying out pyrolysis in the above range, the ferrite oxide catalyst powder where an active metal including magnesium and iron is uniformly dispersed may be prepared.

By calcinating the catalyst powder in the reservoir after conveying the catalyst powder to the reservoir in step (c), purity may increase by purifying the catalyst powder, and accordingly the selectivity and yield of 1,3-butadiene prepared using the catalyst may increase.

As used herein, the term "calcination" means a thermal treatment process causing pyrolysis or phase transition by heating a solid, or a thermal treatment process removing volatile ingredient. By the calcination process, the purity, stability, and activity of the ferrite metal oxide catalyst may increase by removing the moisture, nitrate, etc. remaining on the surface or in the catalyst powder obtained in step (b).

The calcination temperature in step (c) may be 500° C. to 600° C., preferably 530° C. to 570° C., and more preferably 550° C. When the calcination temperature is less than 500° C., effect of increasing the purity of the catalyst may be insignificant, and when the calcination temperature is greater than 600° C., the selectivity of 1,3-butadiene may increase but the yield may sharply decrease.

Also, the calcination in step (c) may be carried out for 1 to 4 hours, and preferably for 1 to 3 hours. When the calcination time is less than 1 hour, the effect of increasing the purity of the catalyst may be insignificant, and when the calcination time is greater than 4 hours, the conversion rate of n-butene may sharply decrease.

The ferrite metal oxide catalyst prepared according to the present invention may be used in the oxidative dehydrogenation of n-butene, thereby producing 1,3-butadiene. Here, the conversion rate of n-butene is 70% to 90%, and the selectivity of 1,3-butadiene is 80% to 90%, which are greatly increased as compared to the conventional preparation method.

Further, the catalyst in powder phase itself may have excellent durability, lifespan, and reaction activity, without a support. However, the ferrite metal oxide catalyst may further include a support, if necessary. In this case, at least one selected from the group consisting of alumina, silica, or silica-alumina may be used as a support, but is not limited thereto.

In the oxidative dehydrogenation of n-butene, a reactant may further include a mixed gas of air and steam, in addition to n-butene. With regard to the mixing ratio of the reactant, the mixing ratio of n-butene:air:steam may be 4 to 12% by volume: 15 to 25% by volume: 45 to 80% by volume, and preferably 5 to 9% by volume: 16 to 30% by volume: 60 to 78% by volume. When the mixing ratio of the reactant deviates from the above range, the reaction activity may decrease or the byproducts may increase.

The amount of the n-butene and air introduced may be controlled by a mass flow controller, and the amount of the steam introduced may be controlled by a minute flow pump.

With regard to the amount of the reactant introduced, n-butene may be introduced in a gas hourly space velocity (GHSV) in range of 100 h$^{-1}$ to 700 h$^{-1}$, preferably in the GHSV in range of 125 h$^{-1}$ to 600 h$^{-1}$, and more preferably in the GHSV in range of 150 h$^{-1}$ to 500 h$^{-1}$. When the GHSV is less than 100 h$^{-1}$, the amount of product per unit time is small, and thus the productivity may be low. When the GHSV is greater than 700 h$^{-1}$, the reaction time for n-butene to react with the catalyst is short, and thus unreacted products may increase and the yield of 1,3-butadiene may decrease.

The oxidative dehydrogenation may be carried out under temperature in range of 300° C. to 500° C., preferably 330° C. to 470° C., and more preferably 350° C. to 450° C. When the reaction temperature is less than 350° C., the activity of the catalyst decreases, and then the partial oxidation reaction may be interfered with. When the reaction temperature is greater than 500° C., the byproducts of C1~C3 may increase or the reactant may be completely oxidized.

Hereinafter, examples of the present invention are described in detail.

EXAMPLE 1

Iron nitrate ($Fe(NO_3)_3 \cdot 6H_2O$, SAMCHUN, 98.5%, 20.5 kg) and magnesium nitrate ($Mg(NO_3)_2 \cdot 6H_2O$, SAMCHUN, 98%, 6.5 kg) are dissolved in distilled water and stirred to prepare a solution containing magnesium and iron in a molar ratio of 2:1. 3 L of the prepared solution is sprayed into a reactor of 750° C. every hour using air (3 atm) as a carrier gas to prepare a catalyst powder. After conveying the prepared catalyst powder to a reservoir, it is calcinated at 500° C. for 3 hours to prepare a magnesium-iron oxide catalyst.

EXAMPLE 2

Except for setting the calcination temperature as 550° C., the magnesium-iron oxide catalyst is prepared under the same conditions as Example 1.

EXAMPLE 3

Except for setting the calcination temperature as 600° C., the magnesium-iron oxide catalyst is prepared under the same conditions as Example 1.

COMPARATIVE EXAMPLE 1

The magnesium-iron oxide catalyst is prepared under the same conditions as Example 1, but the calcination step is omitted.

COMPARATIVE EXAMPLE 2

Except for setting the calcination temperature as 650° C., the magnesium-iron oxide catalyst is prepared under the same conditions as Example 1.

EXPERIMENTAL EXAMPLE 1

Figure 2:
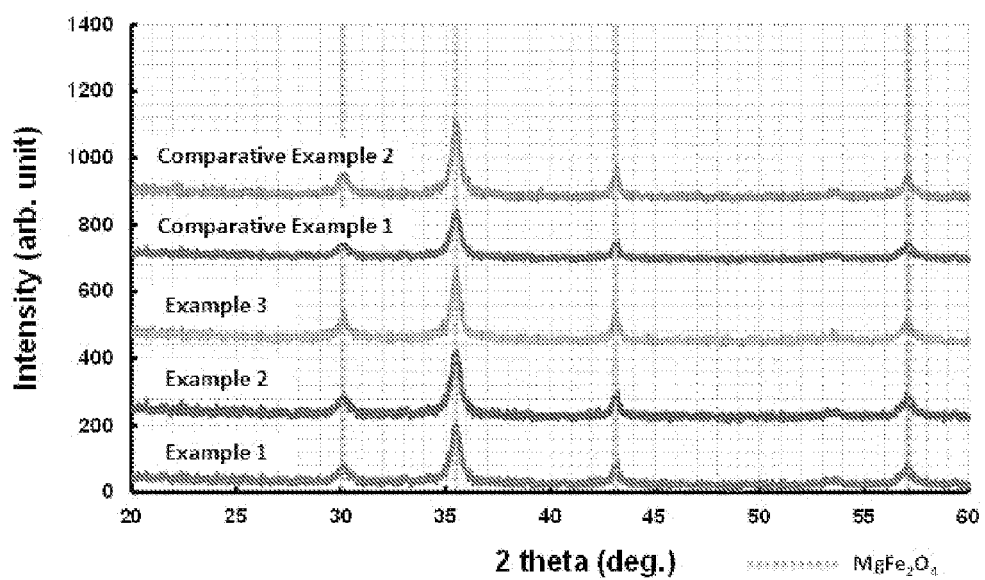
FIG. 2 illustrates X-ray diffraction (XRD) analysis results of ferrite metal oxide catalysts prepared according to embodiments and comparative examples of the present invention.

Analysis of Crystal of Ferrite Metal Oxide Catalyst According to the Preparation Conditions In order to confirm the crystal structure of the magnesium-iron oxide catalysts prepared according to Examples 1~3 and Comparative Examples 1~2, XRD analysis is performed with an X-ray diffraction analyzer (Siemens D-5005, Cuk$\alpha$=1.5418 Å) using a Ni-filter under conditions of 40 kV and 40 mA, and the results are shown in FIG. 2. Referring to FIG. 2, it is confirmed that the crystal structure of the magnesium-iron oxide catalyst is a spinel structure regardless of the preparation conditions of the catalyst.

EXAMPLE 4

Except for setting the calcination time as 2 hours, the magnesium-iron oxide catalyst is prepared under the same conditions as Example 1.

EXAMPLE 5

Except for setting the calcination time as 1 hour, the magnesium-iron oxide catalyst is prepared under the same conditions as Example 1.

COMPARATIVE EXAMPLE 3

Except for setting the calcination temperature as 450° C., the magnesium-iron oxide catalyst is prepared under the same conditions as Example 1.

COMPARATIVE EXAMPLE 4

Except for setting the calcination time as 30 minutes, the magnesium-iron oxide catalyst is prepared under the same conditions as Example 1.

COMPARATIVE EXAMPLE 5

Except for setting the calcination time as 5 hours, the magnesium-iron oxide catalyst is prepared under the same conditions as Example 1.

EXPERIMENTAL EXAMPLE 2

Analysis of Physical Property of Ferrite Metal Oxide Catalyst According to the Preparation Conditions In order to analyze the surface area of the magnesium-iron oxide catalyst prepared according to Examples 1~5 and Comparative Examples 1~5, the surface area is calculated using BET equation after measuring the nitrogen adsorption amount using a BET analyzer (Quantachrome, ASiQ AGC/TCD), and the results are as shown in Table 1 below.

Also, in order to analyze the weight loss of the magnesium-iron oxide catalyst prepared according to Examples 1~5 and Comparative Examples 1~5, the weight loss is measured while raising the temperature from room temperature to 900° C. under air atmosphere using a thermogravimetric analyzer (PerkinElmer, Pyris 6 TGA), and the results are as shown in Table 1 below.

TABLE 1

|  | Surface area ($m^2/g$) | Weight loss (% by weight) |
| --- | --- | --- |
| Example 1 | 92 | 9.0 |
| Example 2 | 84 | 5.6 |
| Example 3 | 70 | 4.7 |
| Example 4 | 78 | 10.0 |
| Example 5 | 65 | 13.0 |
| Comparative Example 1 | 54 | 25.0 |
| Comparative Example 2 | 67 | 3.3 |
| Comparative Example 3 | 63 | 15.8 |
| Comparative Example 4 | 62 | 13.7 |
| Comparative Example 5 | 89 | 6.5 |

Referring to Table 1, the surface area of the magnesium-iron oxide catalysts that goes through the calcination step is 60 to 100 $m^2/g$, while the surface area is less than 60 $m^2/g$ when not going through the calcination step. Thus, it can be understood that the magnesium-iron oxide catalyst that goes through the calcination step has a relatively larger surface area.

Also, the weight loss of the magnesium-iron oxide catalyst that goes through the calcination step is 3 to 16% by weight, while the weight loss when not going through the calcination step is greater than 20% by weight. Thus, it can be understood that the magnesium-iron oxide catalyst that goes through the calcination step has a relatively stable structure.

Comparing Examples 1~3 and Comparative Examples 2 & 3, which go through the calcination step setting the calcination temperature differently, when the calcination temperature is greater than 600° C., the surface area of the catalyst decreases, and when the calcination temperature is less than 500° C., the surface area of the catalyst decreases and the weight loss increases.

Comparing Examples 1, 4 & 5 and Comparative Examples 4 & 5, which go through the calcination step setting the calcination time differently, when the calcination time is less than 1 hour, the surface area of the catalyst decreases and the weight loss increases.

As such, it can be understood that the magnesium-iron oxide catalyst prepared by going through the calcination step setting the calcination temperature to 500° C. to 600° C. and the calcination time to at least 1 hour has higher activity and stable structure than a catalyst that does not go through a calcination step because it has a large surface area and small weight loss.

EXPERIMENTAL EXAMPLE 3

Figure 3:
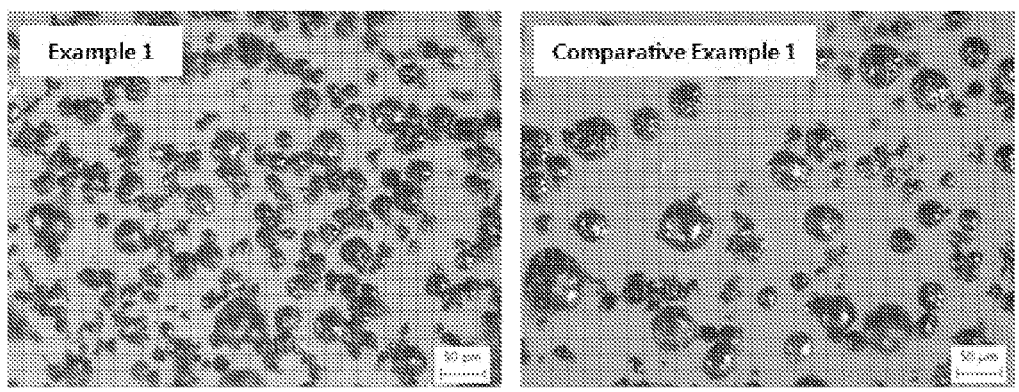
FIG. 3 illustrates imaging microscope images of ferrite metal oxide catalysts according to one embodiment and one comparative example of the present invention.

Analysis of Particle Size and Shape of Ferrite Metal Oxide Catalyst According to the Preparation Conditions In order to analyze the particle size and shape of the magnesium-iron oxide catalysts prepared according to Example 1 and Comparative Example 1, the image is observed using an imaging microscope (ICAMSCOPE, SOMTECH), and the results are shown in FIG. 3.

Referring to FIG. 3, it is confirmed that the particle size of the catalyst powder prepared according to Example 1 is smaller than that of the Comparative Example 1, and the surface area is larger. Thus, the results are the same as the results of Experimental Example 2.

EXPERIMENTAL EXAMPLE 4

Analysis of Reactivity of 1,3-butadiene According to the Preparation Conditions of Ferrite Metal Oxide Catalyst The magnesium-iron oxide catalyst prepared according to Examples 1~5 and Comparative Examples 1~5 is filled in a stainless reactor, and activated at 370° C. while introducing air. A mixed gas of the reactant where the mixing ratio of C4 mixture (n-butene):air: steam is 5.2% by volume: 17.2% by volume: 77.6% by volume is flowed in a gas hourly space velocity (GHSV) of 400 h$^{-1}$ to pass through the reactor, to prepare 1,3-butadiene. The conversion rate of n-butene, selectivity of 1,3-butadiene, and yield of 1,3-butadiene are calculated using the following Equations 1~3, respectively, and the results are shown in Table 2 below.

Conversion rate of n-butene $$\text{Conversion rate of n-butene (\%)} = \frac{\text{weight of n-butene reacted}}{\text{weight of n-butene introduced}} \times 100 \quad \text{[Equation 1]}$$

Selectivity of 1,3-butadiene $$\text{Selectivity of 1,3-butadiene (\%)} = \frac{\text{weight of 1,3-butadiene created}}{\text{weight of n-butene reacted}} \times 100 \quad \text{[Equation 2]}$$

Yield of 1,3-butadiene $$\text{Yield of 1,3-butadiene (\%)} = \frac{\text{weight of 1,3-butadiene created}}{\text{weight of n-butene introduced}} \times 100 \quad \text{[Equation 3]}$$

TABLE 2

| | Conversion rate of n-butene (%) | Selectivity of 1,3-butadiene (%) | Yield of 1,3-butadiene (%) |
|---|---|---|---|
| Example 1 | 79.7 | 86.0 | 68.5 |
| Example 2 | 78.9 | 87.1 | 68.7 |
| Example 3 | 72.5 | 89.1 | 64.6 |
| Example 4 | 81.2 | 84.8 | 68.9 |
| Example 5 | 82.1 | 82.5 | 67.7 |
| Comparative Example 1 | 86.0 | 81.6 | 70.2 |
| Comparative Example 2 | 67.5 | 88.4 | 59.7 |
| Comparative Example 3 | 84.8 | 81.4 | 69.0 |
| Comparative Example 4 | 84.1 | 81.7 | 68.7 |
| Comparative Example 5 | 76.5 | 85.5 | 65.4 |

Referring to Table 2, the selectivity of 1,3-butadiene is at least 82% when using the magnesium-iron oxide catalyst prepared by going through the calcination step, while the selectivity is less than 82% when not going through the calcination step. Thus, it can be understood that the activity of the magnesium-iron oxide catalyst prepared by Examples 1-5 is relatively excellent.

Comparing the results of Examples 1~3 and Comparative Examples 2 & 3, which go through the calcination step setting the calcination temperature differently, when the calcination temperature is less than 500° C. (Comparative Example 3), the selectivity of 1,3-butadiene decreases compared with the case of not going through the calcination step (Comparative Example 1), and when the calcination temperature is greater than 600° C. (Comparative Example 2), the conversion rate of n-butene and the yield of 1,3-butadiene sharply decrease.

Comparing the results of Examples 1, 4 & 5 and Comparative Examples 4 & 5, which go through the calcination step setting the calcination time differently, when the calcination time is less than 1 hour (Comparative Example 4), the selectivity of 1,3-butadiene decreases compared with the case of not going through the calcination step (Comparative Example 1), and when the calcination time is greater than 4 hours (Comparative Example 5), the conversion rate of n-butene and the yield of 1,3-butadiene sharply decrease.

As such, it can be understood that the conversion rate of n-butene, the yield of 1,3-butadiene, and the selectivity of 1,3-butadiene may increase when preparing 1,3-butadiene using the magnesium-iron oxide catalyst prepared by additionally going through the calcination step and controlling the calcination temperature and time to be 500° C. to 600° C. and 1 hour to 4 hours, respectively.

The above descriptions of the present invention are provided as examples, and it will be apparent to those skilled in the art that various modifications can be easily made to the above-described exemplary embodiments of the present invention without departing from the spirit or scope of the invention. Thus, it should be understood that the exemplary embodiments described above are merely examples, but not limited. For example, the components explained in a single type can be realized separately, and components to be explained as separated may be realized as components binding to each other. The scope of the present invention is represented by the following claims, and it should be construed that all modifications or modified forms deduced from the meaning and scope, and an equivalent concept of the claims are included in the scope of the present invention.

What is claimed is:

1. A method for preparing a ferrite metal oxide catalyst, comprising:
   (a) preparing a precursor solution by dissolving a magnesium nitrate precursor and an iron nitrate precursor in a polar solvent;
   (b) forming a catalyst powder by spray-pyrolyzing the precursor solution into a reactor using a carrier gas; and
   (c) calcinating the catalyst powder in a reservoir after conveying the catalyst powder to the reservoir,
   wherein a pyrolysis temperature in step (b) is 700° C. to 800° C., and
   wherein a calcination temperature in step (c) is 500° C. to 600° C. wherein the magnesium nitrate precursor and the iron nitrate precursor in step (a) are mixed so that a molar ratio of magnesium to iron is in the range of 1.5:1 to 2.5:1.

2. The method according to claim 1, wherein the magnesium nitrate precursor and the iron nitrate precursor in step (a) are magnesium nitrate and iron nitrate, respectively.

3. The method according to claim 1, wherein the polar solvent in step (a) is distilled water.

4. The method according to claim 1, wherein the carrier gas in step (b) is air.

5. The method according to claim 4, wherein a pressure of the air in step (b) is 2 to 4 atm.

6. The method according to claim 1, wherein the calcination in step (c) is carried out for 1 to 4 hours.

* * * * *